(12) United States Patent
Byrum et al.

(10) Patent No.: US 9,649,214 B2
(45) Date of Patent: May 16, 2017

(54) DETACHABLE ANTENNA FOR REMOTE BAND

(75) Inventors: Randal T. Byrum, South Lebanon, OH (US); Sean P. Conlon, Loveland, OH (US); Alec J. Ginggen, Plymouth, MA (US); Bret W. Smith, Kings Mill, OH (US); Dean L. Garner, Cincinnati, OH (US); Daniel F. Dlugos, Jr., Middletown, OH (US)

(73) Assignee: ETHICON ENDO-SURGERY, INC., Cincinnati, OH (US)

( * ) Notice: Subject to any disclaimer, the term of this patent is extended or adjusted under 35 U.S.C. 154(b) by 2351 days.

(21) Appl. No.: 12/557,836

(22) Filed: Sep. 11, 2009

(65) Prior Publication Data

US 2011/0063176 A1 Mar. 17, 2011

(51) Int. Cl.
*A61F 5/00* (2006.01)

(52) U.S. Cl.
CPC .................................. *A61F 5/0059* (2013.01)

(58) Field of Classification Search
CPC .... A61F 5/0053; A61F 5/0066; A61F 5/0059; A61F 2002/48; A61F 5/003; A61F 5/0003; A61F 5/0063
USPC ..................... 600/37; 606/139–141, 151, 157
See application file for complete search history.

(56) References Cited

U.S. PATENT DOCUMENTS

| | | | | |
|---|---|---|---|---|
| 2005/0143765 | A1* | 6/2005 | Bachmann et al. | 606/157 |
| 2007/0213836 | A1* | 9/2007 | Paganon | 623/23.64 |
| 2009/0062825 | A1* | 3/2009 | Pool et al. | 606/157 |

FOREIGN PATENT DOCUMENTS

| | | |
|---|---|---|
| JP | H02-186571 A | 7/1990 |
| JP | H04-223076 A | 8/1992 |
| JP | 2003-517877 A | 6/2003 |
| JP | 2008-515582 A | 5/2008 |

* cited by examiner

*Primary Examiner* — Christine H Matthews
(74) *Attorney, Agent, or Firm* — Welsh Flaxman & Gitler LLC

(57) ABSTRACT

An apparatus for regulating the functioning of a patient's organ or duct. The apparatus includes an elongated member having first end and second ends. A fastener is disposed on the first end of the elongated member. The fastener is configured to engage the second end of the elongated member so that the elongated member forms a ring around the organ or duct. A tension element is slidably disposed within the elongated member. A drive element is associated with and engaging the tension element for causing the tension element to control the tension applied by the elongated member against a patient's body organ or duct. An antenna/controller pod is releasably coupled to the elongated member for control of the drive element.

7 Claims, 9 Drawing Sheets

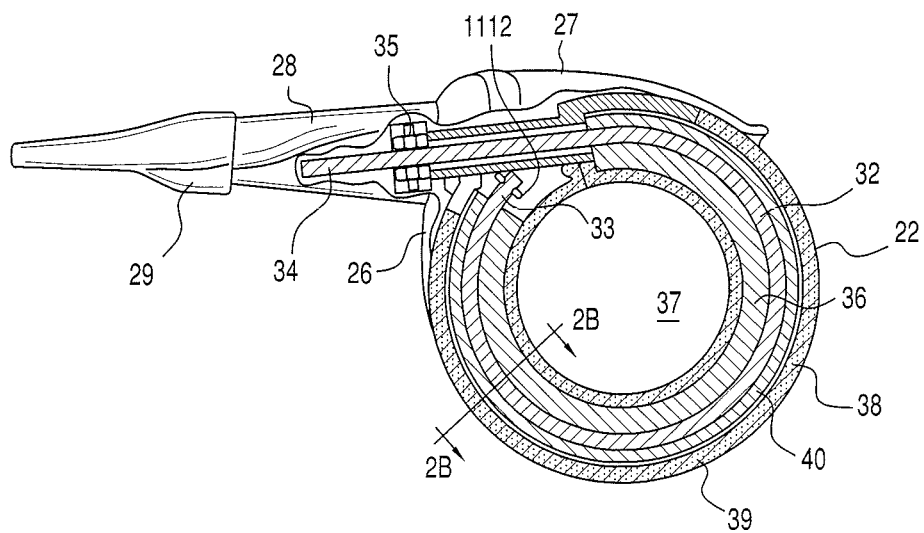
FIG. 2A
FIG. 2B
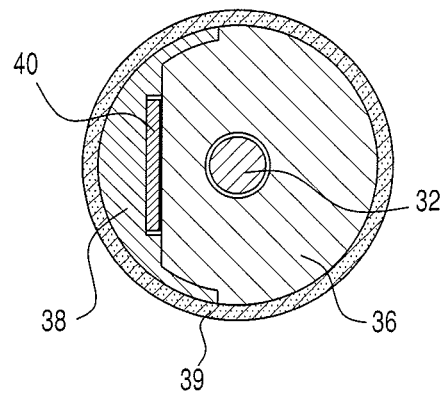

FIG. 8
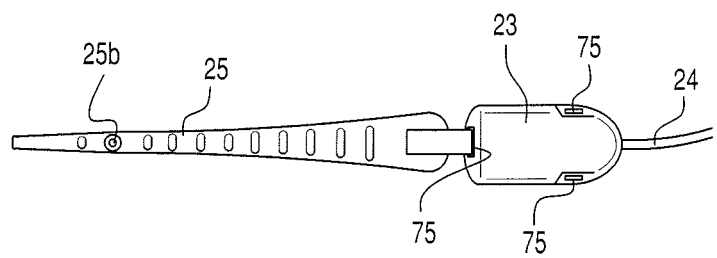
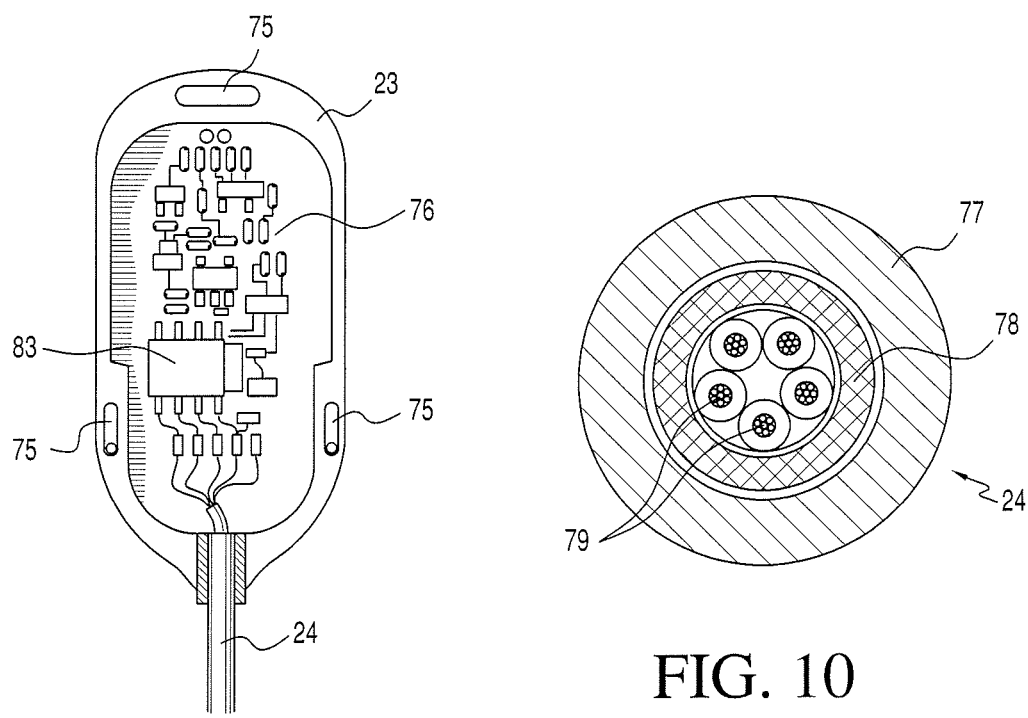
FIG. 10
FIG. 9

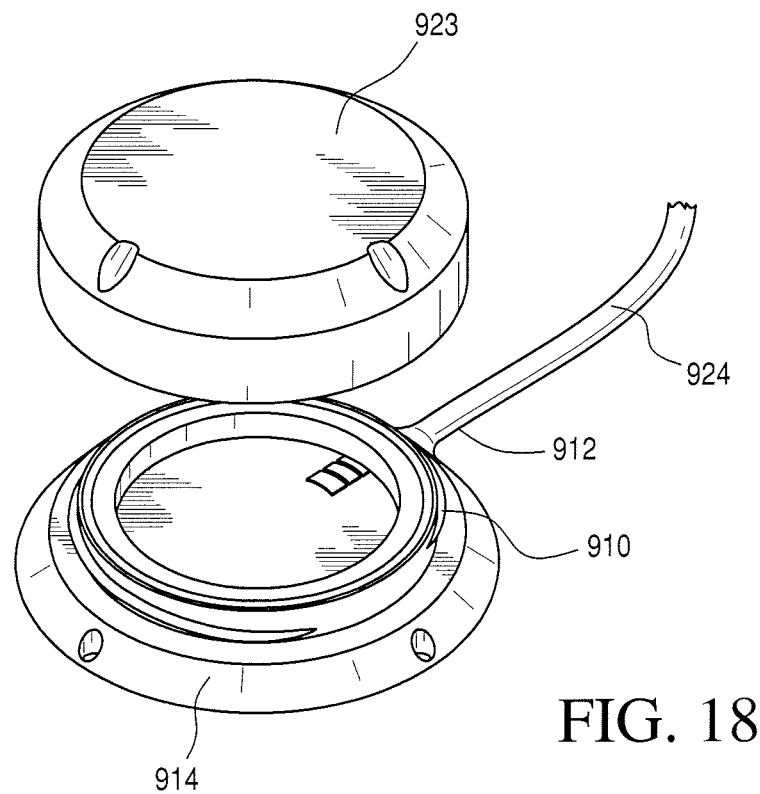
FIG. 18
FIG. 19
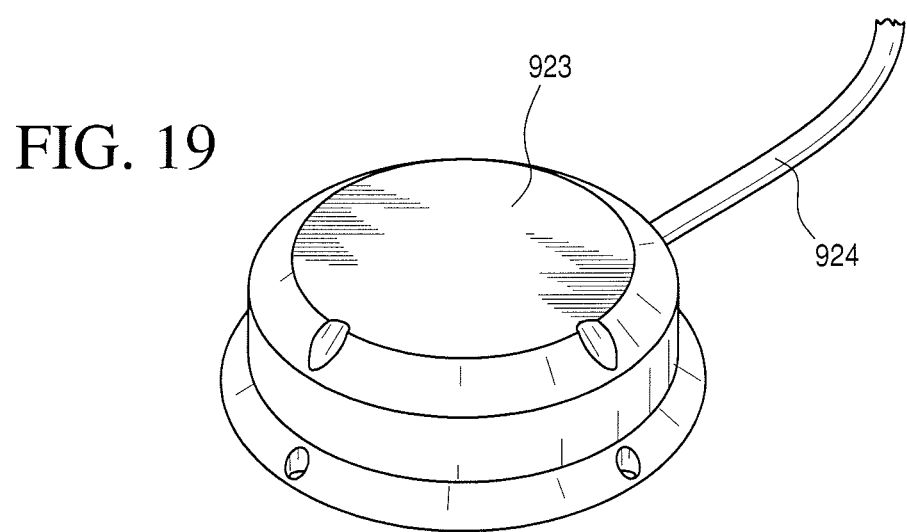

DETACHABLE ANTENNA FOR REMOTE BAND

BACKGROUND OF THE INVENTION

1. Field of the Invention

This invention relates to laparoscopic implants designed to be implanted in the body of a patient around a biological organ having a pouch or duct to regulate functioning of the organ or duct. More specifically, the present invention is directed to an implantable telemetrically-powered and controlled ring having a detachable antenna suitable for use as a gastric band to treat obesity or as an artificial sphincter.

2. Description of the Related Art

Obesity refers to a body weight that exceeds the body's skeletal and physical standards. One well recognized parameter used to measure obesity is Body Mass Index (BMI) because it takes into account patient height and not just weight. BMI is calculated by dividing weight by height squared and is expressed in kg/m2.

Obesity is usually defined as a BMI of 30 kg/m2 or greater, and is further broken down into Class I (BMI of 30-34.9 kg/m2), Class II (BMI of 35-39.9 kg/m2) also called severe obesity, and Class III (BMI of 40 kg/m2 or greater), also called extreme obesity. Obesity is considered "morbid" when the BMI is over 40 (extreme obesity) or the BMI is over 35 (severe obesity) and serious comorbidities are present.

Obesity is well recognized as a serious health problem, and is associated with numerous health complications, ranging from non-fatal conditions to life-threatening chronic diseases. Surgical intervention generally is the treatment of choice for patients afflicted with morbid obesity. Such intervention not only mitigates the myriad health problems arising from overweight, but may also reduce the risk of early death of the patient. Left untreated, morbid obesity may reduce a patient's life expectancy by ten to fifteen years.

Morbidly obese patients as a group are poorly adapted to attain sustainable long-term weight loss using non-surgical approaches, such as strict diets combined with exercise and behavioral modification, even though such methods are acknowledged to be the safest. For this reason, there is a continuing need for direct intervention to provide effective, long-term treatments for morbid obesity. Three main surgical procedures are currently in use: Roux-en-Y Gastric Bypass ("RYGB"), Vertical Banded Gastroplasty ("VBG") and Adjustable Gastric Banding ("AGB").

In RYGB a small stomach pouch is created and a Y-shaped section of the small intestine is attached to the pouch so that food bypasses the lower stomach, the duodenum and the first portion of the jejunum. The RYGB procedure is both restrictive, in that the small pouch limits food intake and malabsorptive, in that the bypass reduces the amount of calories and nutrients the body absorbs.

VBG employs a non-adjustable synthetic band and staples to create a small stomach pouch. AGB employs a constricting synthetic ring that is placed around the upper end of the stomach to create an artificial stoma within the stomach. The band is filled with saline solution and is connected to small reservoir/access-port located under the skin of the abdomen. The AGB band may be inflated, thereby reducing the size of the stoma, or deflated, thus enlarging the stoma, by puncturing the access-port with a needle and adding or removing saline solution. Both VBG and AGB are purely restrictive procedures, and have no malabsorptive effect.

An example of the AGB technique is described, for example, in U.S. Pat. No. 5,074,868 to Kuzmak. As described in the '868 patent, a flexible band of elastomeric material is implanted around the stomach to form a closed loop defining a fixed pre-established diameter. The body of the flexible band includes an expandable chamber, which is linked via a tube to a subcutaneous injection port. Fluid may be introduced into the injection port using a syringe to add or remove fluid from the expandable chamber and thus vary the internal diameter of the band and the diameter of the stoma. In this way, expansion of the chamber, in combination with the pre-established and fixed diameter of the band, permits adjustment of the stoma diameter and thus regulation of the quantity of food ingested.

The injection port is the source of many of the problems encountered with the hydraulic gastric bands, including infection, damage to the tube due to imprecise puncturing with the needle, discomfort to the patient created by the port and difficulty in locating the port (often necessitating the use of x-ray to determine the location and orientation of the port).

In addition, although the injection port makes it possible to make limited adjustments to the diameter of the ring without major surgical intervention, installation of the band may be accompanied by intolerance phenomena, such as vomiting. This drawback may arise from various causes, including too great a reduction in the diameter of the stoma, ineffective action of the band due to too great a stoma diameter, obstruction, infection or local or general inflammation.

Accordingly, it sometimes is necessary to re-operate, either to relieve the patient or to adjust or change the previously-implanted band. In such cases, the previously-implanted band must be cut and either removed or replaced, during operations that are difficult to carry out, difficult for the patient to tolerate and costly.

U.S. Pat. No. 5,938,669 to Klaiber et al. addresses some of the issues arising from use of an injection port, and describes a gastric band that is adjusted using a remote control in a non-invasive manner. The device includes a control box that is implanted in the body of the patient and coupled to the gastric band. The control box includes a battery-operated electric pump and valve that are coupled between an expandable chamber and a fluid reservoir. The control box also contains a radiofrequency transceiver and microprocessor, which are arranged to communicate with an external remote control to control operation of the pump to add or remove fluid from the reservoir to the expandable chamber, thereby selectively varying the diameter of the stoma opening. The external remote control is operated by a physician.

All of the foregoing surgical techniques involve major surgery and may give rise to severe complications. Recent developments have focused on the use of laparoscopic implantation of the gastric ring to minimize patient discomfort and recuperation time.

In view of the foregoing, it would be desirable to provide apparatus and methods for regulating functioning of a body organ or duct that provides high precision in a degree of constriction imposed upon the organ or duct, without the drawbacks associated with the use of previously-known injection ports.

SUMMARY OF THE INVENTION

It is, therefore, an object of the present invention to provide an apparatus for regulating the functioning of a patient's organ or duct. The apparatus includes an elongated member having a first end and a second end. A fastener is disposed on the first end of the elongated member. The fastener is configured to engage the second end of the elongated member so that the elongated member forms a ring around the organ or duct. A tension element is slidably disposed within the elongated member. A drive element is associated with and engaging the tension element for causing the tension element to control the tension applied by the elongated member against a patient's body organ or duct. An antenna/controller pod is releasably coupled to the elongated member for control of the drive element.

It is also an object of the present invention to provide an apparatus wherein an antenna cable connects the antenna/controller pod to the elongated member.

It is another object of the present invention to provide an apparatus wherein the antenna cable includes a proximal end which is selectively secured to a distal end of the antenna/controller pod in a manner maintaining electrical connections between the antenna/controller pod and the antenna cable.

It is a further object of the present invention to provide an apparatus wherein the distal end of the antenna/controller pod includes a first attachment member having a housing sheath with a coupling member and the proximal end of the antenna cable includes a second attachment member having a housing sheath with a coupling member, the first attachment member being shaped and dimensioned for selective attachment to the second attachment member to create a fluid tight seal protecting electrical components contained within the housing sheath of the first attachment member and the housing sheath of the second attachment member.

It is also an object of the present invention to provide an apparatus wherein the antenna cable includes an environmentally sealed housing supporting a center portion housing wires from the antenna cable and connection members for receiving connection members of the antenna/controller pod.

It is another object of the present invention to provide an apparatus wherein the connection members of antenna cable are female receptacles and the connection members of the antenna/controller pod are male pins.

It is a further object of the present invention to provide an apparatus wherein an outer wall of the housing of the antenna cable is provided with projections shaped and dimensioned for engagement with a slot formed along a coupling member of the antenna/controller pod.

It is also an object of the present invention to provide an apparatus wherein the center portion of the antenna cable is secured to the housing such that it is free to rotate with respect to the housing.

It is another object of the present invention to provide an apparatus wherein the antenna cable is threadingly connected to the antenna/controller pod.

It is a further object of the present invention to provide an apparatus wherein the antenna cable is provided with a retaining base at its proximal end and the antenna/controller pod is selectively screwed upon the retaining base.

Still a further object is to provided a method for implanting an apparatus for regulating the functioning of a patient's organ or duct including: a) inserting an antenna/controller pod into the patient through a first body opening remote from the patient's organ or duct to be regulated; b) inserting through a second body opening spaced from the first body opening an elongated restrictive device comprising an elongated member having first end and second ends with a fastener disposed on the first end of the elongated member, the fastener configured to engage the second end of the elongated member so that the elongated member forms a ring around the organ or duct to be regulated, a tension element disposed for movement within the elongated member, and a drive element associated with and engaging the tension element for causing the tension element to control the tension applied by the elongated member against the patient's body organ or duct; and c) connecting in situ the antenna/controller pod via a cable to the drive element of the elongated restrictive device in order to control movement of the tension element.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 2A and 2B are, respectively, a schematic diagram, partly in cross-section, of the gastric band of FIG. 1 and a sectional view taken along line 2B-2B of FIG. 2A.

FIG. 8 is a perspective view of the antenna/controller pod of the present invention.

FIG. 9 is a cut-away view of the interior of the implantable antenna/controller pod of FIG. 8.

FIG. 10 is a cross-sectional view of the antenna cable of FIG. 9.

FIGS. 11 to 20 disclose various embodiments for selectively securing the antenna/controller pod to the antenna cable.

FIG. 20 is a detailed view of the signal strength indicator portion of the remote control of FIG. 1.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Figure 1:
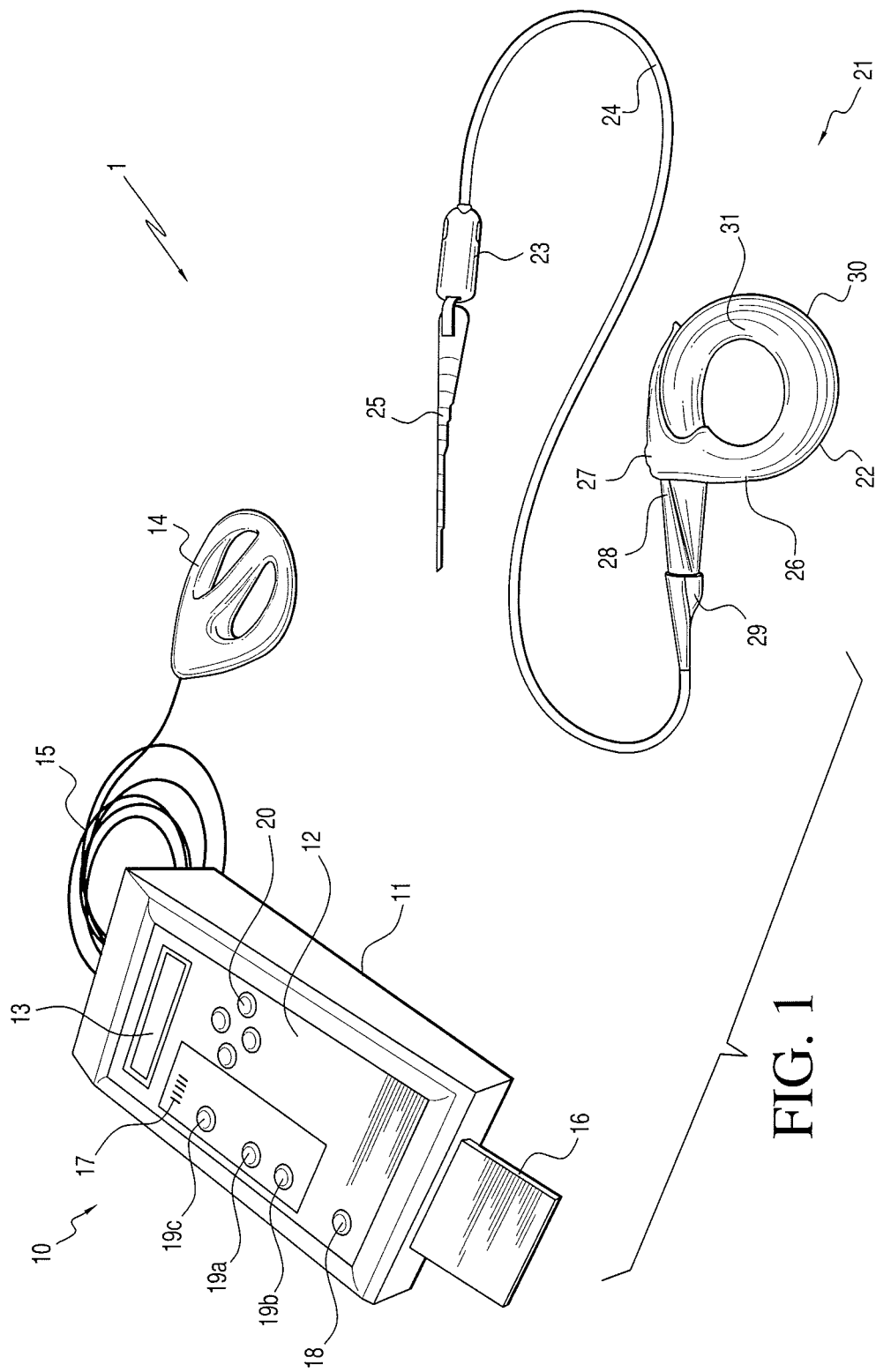
FIG. 1 is a perspective view of an exemplary banding system of the present invention including an external control and implantable ring.

Referring now to FIG. 1, the implantable restriction system 1 of the present invention is described. The banding system 1 includes an external control 10 and implantable gastric band 21. In the following description reference will be made, by way of illustration, to a gastric band 21 in the form of a ring 22 designed to be implanted around the stomach to selectively adjust the diameter of the opening of the stoma, and thereby control food intake. Such regulation has the effect of creating a feeling of satiety in the patient after relatively little food is consumed, and provides an effective treatment for morbid obesity.

It is to be understood, however, that the present invention is in no way limited to gastroplasty, but on the contrary, advantageously may be applied to regulate the functioning of other body organs or ducts, such as in the treatment of gastro-esophageal reflux disease, urinary or fecal incontinence, colostomy, ileostomy or to regulate blood flow in connection with isolated organ perfusion for treatment of cancer. When applied in the treatment of urinary continence, the implantable portion of the present banding system 1, in particular, the elongated member in the form of a ring 22 will be implanted around the bladder or urinary tract, while in the case of fecal incontinence, the ring 22 may be implanted around a portion of the gastro-intestinal tracts, such as anal structures of the intestine. With this in mind, the present banding system is MRI compatible and all elements thereof are non-ferro-magnetic.

As discussed above, the present invention relates to an implantable restriction system. A preferred embodiment of the implantable restriction system is disclosed herein within reference to a gastric band used in restricting the effective size of the stomach for application in bariatric procedures. As such, the implantable restriction system of the present invention is referred to as a gastric band or ring throughout the present disclosure, although those skilled in the art will appreciate the concepts underlying the present invention may be applied in a variety of implantable restriction devices as briefly discussed above.

With respect to FIG. 1, the self-contained external control 10 comprises a housing 11 having a control panel 12 and a display screen 13. The external control 10 includes a digital signal processor and may be battery-powered or powered using an external power supply, e.g., connected to an electric wall outlet. An external antenna 14 is coupled to the external control 10 via a cable 15. The external control 10 includes a controller (such as a microprocessor) that controls the emission of radiofrequency signals to the gastric band 21 to both control and power operation of the gastric band 21.

The external control 10 accepts a patient microchip card 16, which corresponds to the specific gastric band 21 implanted in the patient, and stores data, such as the implant identification number, adjustment parameters (e.g., upper and lower limits of an adjustment range, etc.) and information regarding the last adjustment position of the ring 22. The external control 10 as shown in FIG. 1 includes a signal strength indicator 17, as described in more detail below with respect to FIG. 20, an ON/OFF button 18, an OPEN button 19a, a CLOSE button 19b, a COUPLING button 19c and a menu options panel 20.

During use of the present banding system 1, the physician need only turn on external control 10 using the ON/OFF button 18, position the external antenna 14 over the patient's chest above antenna/controller pod 23, check the coupling by depressing the COUPLING button 19c, and when the coupling is sufficient, adjust the degree of constriction using the OPEN button 19a or the CLOSE button 19b to control the effective circumference of the ring 22 in a manner discussed below in greater detail. The diameter of the band is continually displayed on the display screen 13 with a precision of about 0.1 mm for the entire range of diameters of the ring 22, e.g., from 19 mm fully closed to 29 mm fully opened.

Still referring to FIG. 1 and as briefly mentioned above, the gastric band 21 of the present invention includes a ring 22 coupled to an implantable antenna/controller pod 23 via an antenna cable 24. The antenna/controller pod 23 includes a removable tag 25 that may be used to laparoscopically position the ring 22. The ring 22 includes a first end 26 having a clip 27 that slides over and positively engages a second end 28 of the ring 22.

Figure 4:
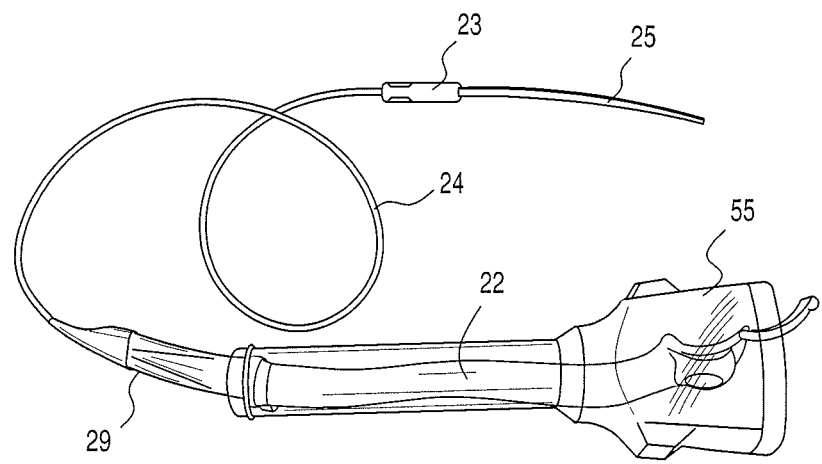
FIG. 4 is a perspective view of the ring of FIG. 1 straightened and inserted within a standard 18 mm trocar.

As described in detail below, the ring 22 is configured to be straightened to pass through the lumen of a commercially available 18 mm trocar for delivery to a patient's abdomen (see FIG. 4). The tag 25, antenna/controller pod 23 and antenna cable 24 then are passed through a clip 27 to form the gastric band 21 into a substantially circular ring 22 around an upper portion of the patient's stomach, thereby reducing the diameter of the opening of the stomach. In its undeformed shape, the gastric band 21 assumes a circular arc configuration that facilitates positioning of the gastric band 21 around the stomach and also in self-guiding the clipping procedure.

Referring to FIGS. 2A and 2B, the ring 22 of the present invention comprises a flexible tubular band having a smooth, flexible and elastic membrane, thus ensuring atraumatic contact with the patient's stomach tissue that is easily tolerated. When engaged with a dorsal element 38, the membrane 39 is stretched by an appropriate factor (i.e., 20%-40%), so that when the ring 22 is in it's fully closed position, little or no wrinkling appears on the membrane surface. The ring 22 has approximately the shape of a torus of revolution of substantially cylindrical cross-section. Alternatively, the ring 22 may have any other suitable cross-section, including rectangular. The housing 29 on the second end 28 of the gastric band 21, the clip 27 on the first end 26 of the gastric band 21 and the dorsal peripheral portion 30 of the gastric band 21, preferably comprise a biocompatible material such as silicone. An interior portion 31 of the ring 22 may be constructed in a variety of manners as discussed below in greater detail to permit engagement with the tissue without bunching or ripples, and, as also discussed below in greater detail, may be covered in various manners to enhance the ring/tissue interface and protect the ring 22.

Still referring to FIGS. 2A and 2B, the internal structure of the ring 22 is described. In particular, and as depicted in FIG. 2A, the ring 22 includes a flexible tension element 32 having a fixed end 33 mounted to the first end 26 of the ring 22 and a free end 34 that is engaged with a motor-driven drive element 35 and extends into a cavity in the housing 29. The tension element 32 is slidingly disposed within a substantially cylindrical tube of a compressible material 36, e.g., ePTFE, as illustrated in FIG. 2B, so that when the tension element 32 is pulled through the drive element 35, the compressible material 36 is compressed and the diameter of opening 37 is reduced. The compressible material 36 is preferably surrounded on its dorsal face with a flexible, but sturdier elastomeric material, such as a silicone dorsal element 38. Both the compressible material 36 and the silicone dorsal element 38 preferably are enclosed within a membrane of elastomeric biocompatible material 39, as shown in FIG. 2B, to prevent tissue in-growth between the ePTFE tube 36 and the silicone dorsal element 38. A membrane 39 may be affixed to the dorsal element 38 using a biocompatible glue to prevent leakage in case of accidental puncture on the dorsal surface.

Figure 3:
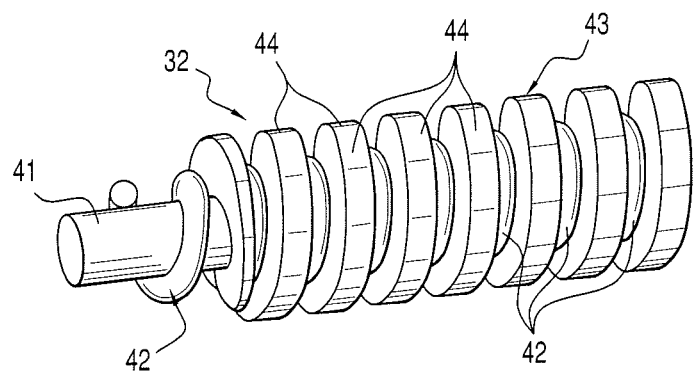
FIG. 3 is a partial perspective view of a screw thread portion of the tension element of the present invention.

Referring now to FIG. 3, the tension element 32 in accordance with a first embodiment is described. This tension element is disclosed in detail in U.S. Patent Application Publication No. 2005/0143766, which is incorporated herein by reference. Briefly, the tension element 32 has sufficient flexibility to permit it to be formed into a substantially circular shape of the ring 22, while also being able to transmit the force necessary to adjust the ring diameter. The tension element 32 therefore comprises a flexible core 41, preferably a metal alloy wire of circular cross section, on which is fixed, and wound coaxially, at least one un-joined coil spring which defines the screw thread pitch.

As shown in FIG. 3, the tension element 32 preferably comprises two un-joined coil springs that form a screw thread: a first spring 42, wound helicoidally along the flexible core 41, and a second spring 43 of greater exterior diameter. The second spring 43 preferably comprises coils 44 of rectangular transverse section, so as to delineate a flat external generatrix. The first spring 42 is interposed between coils 44 of the second spring 43 to define and maintain a substantially constant square screw thread pitch, even when the tension element 32 is subjected to bending.

As a consequence of the foregoing arrangement, the ability of the tension element 32 to maintain a substantially constant thread pitch, when subjected to bending, confers great precision on adjustments of the ring 22. The maintenance of the threaded pitch is especially problematic when it is realized that as the tension element 32 is drawn through the drive element 35, an ever-increasing curvature (that is, a reduction in the radius of curvature) is imposed on the remaining portion of the tension element 32 which in turn alters the effective thread pitch along the length of the tension element 32. However, because the foregoing arrangement of un-joined coils maintains a substantially constant screw thread pitch, the energy needed to drive the drive element 35 remains low and the efficiency of energy transmission resulting from the use of a square screw thread pitch remains high. In addition, the use of a square screw thread pitch guarantees a stable adjustment position even when the drive element is unpowered.

Figure 5:
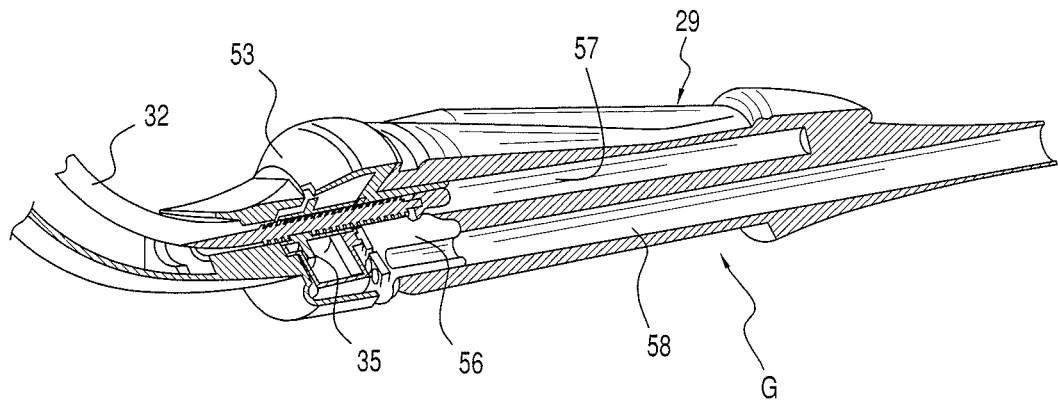
FIG. 5 is a cross-sectional view of an elastomeric housing of the gastric band depicting the path of the antenna wire and cavity that accepts the tension element.

Referring now to FIG. 5, the housing 29 of the free end of the ring 22 is described. The housing 29 comprises an elastomeric material, such as silicone, having a recessed portion 56, a tension element cavity 57 and a cable lumen 58. The recessed portion 56 is configured to accept the drive element housing 53, so that as the tension element 32 is drawn through the drive element 35 to extend into the tension element cavity 57. A cable lumen 58 extends through the housing 29 so that the antenna cable 24 may be coupled to the drive element 35. The housing 29 preferably may be grasped in area G using atraumatic laparoscopic graspers during manipulation of the gastric band 21.

Figure 6:
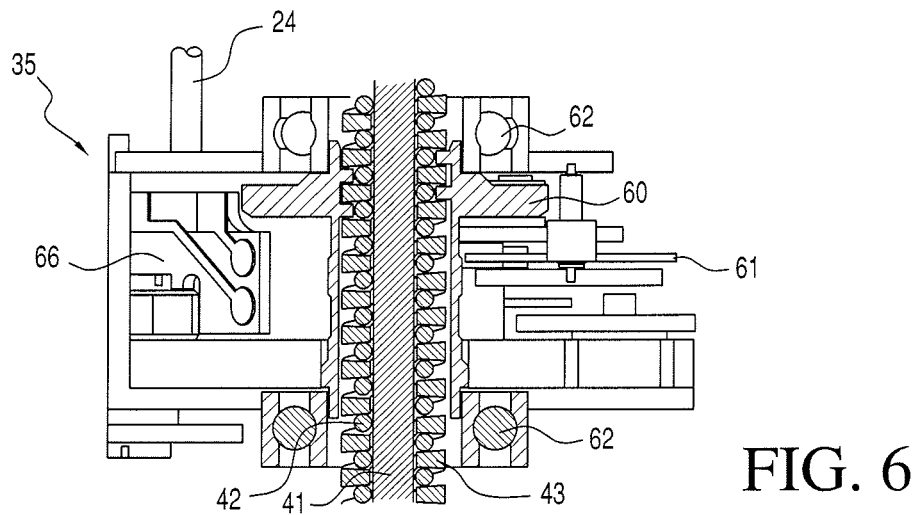
FIG. 6 is a cross-sectional view depicting the construction of the drive element.
Figure 7:
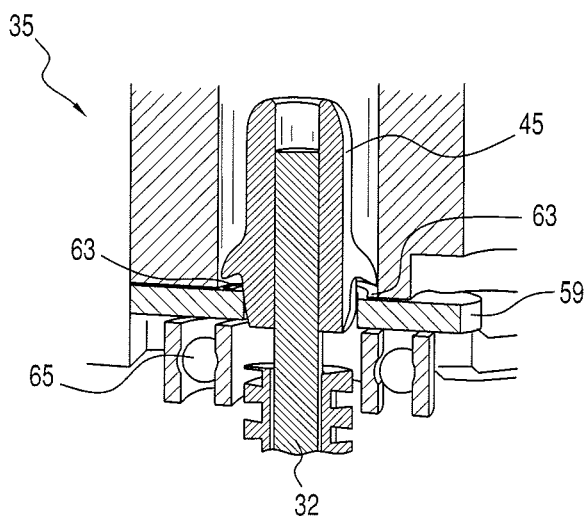
FIG. 7 is a cross-sectional view depicting the construction of the reference position switch.
Figure 11:
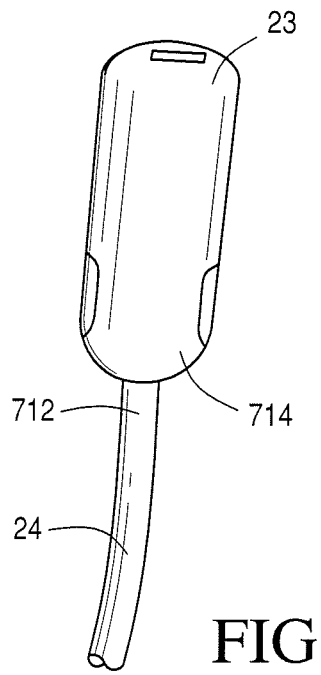
Figure 12:
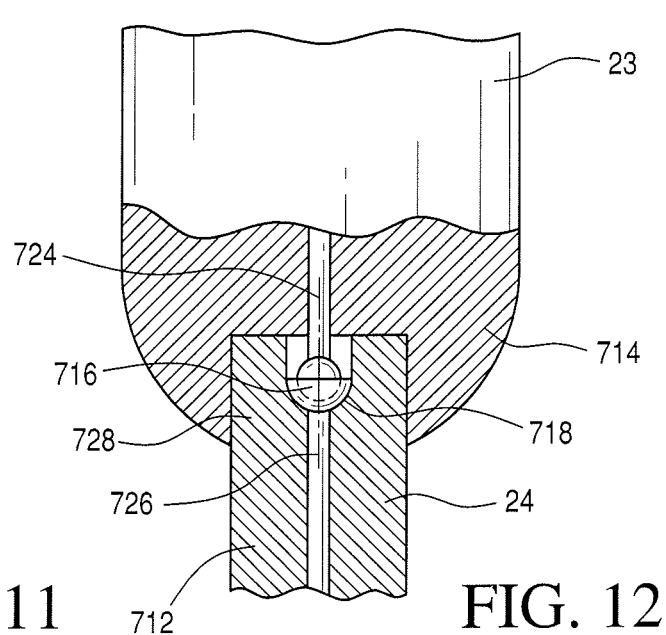
Figure 13:
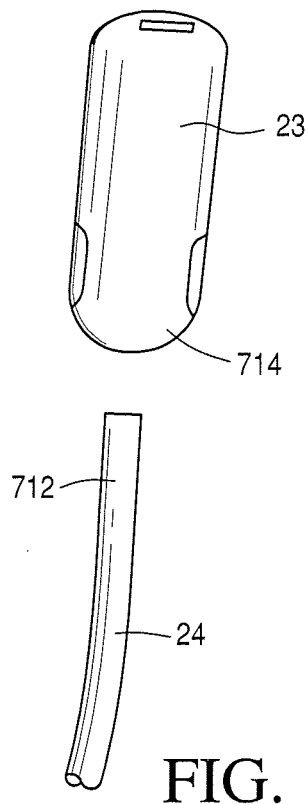
Figure 14:
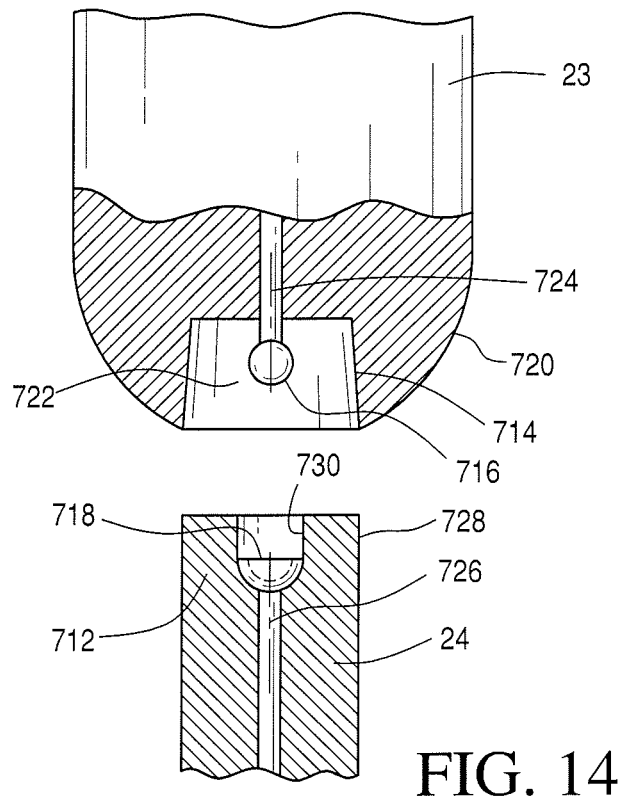

With respect to FIGS. 6 and 7, the drive element 35 used in conjunction with the tension element 32, includes a motor 66 coupled to the antenna cable 24 that drives the nut 60 through the gears 61. As with the various embodiments present throughout the present disclosure, the motor may take a variety of forms including but not limited to a stepper motor and piego motor. The nut 60 is supported by upper and lower bearings 62 to minimize energy losses due to friction. The nut 60 is self-centering, self-guiding and provides high torque-to-axial force transfer. The drive element is disclosed in greater detail with reference to U.S. Patent Application Publication No. 2005/0143766, which is incorporated herein by reference.

Referring now to FIG. 7, the reference position switch of the present banding system 1 is described. Because the drive element 35 of the present banding system employs a nut 60 driven by a stepper motor, there is no need for the system to include a position sensor or encoder to determine the length of the tension element 32 drawn through the drive element 35. Instead, the diameter of the ring 22 may be directly computed as a function of the screw thread pitch and the number of rotations of the nut 60. To ensure an accurate calculation of the degree of restriction imposed by the gastric ring 22, however, it is desirable to provide at least one reference point.

This reference datum is accomplished in the gastric ring 22 of the present invention using a reference position switch that is activated when the ring 22 is moved to its fully open position. The crimped cap 45 on the free end of the tension element 32 serves this function by contacting electrical traces 63 on the printed circuit board 59 (and also limits elongation of the screw thread). The circuit board 59 is disposed just above the bearing 65, which forms part of the drive element 35. When the crimped cap 45 contacts the traces 63 it closes a switch that signals the implantable controller that the gastric ring 22 is in the fully open position.

With respect to FIGS. 8 and 9, the antenna/controller pod 23 of the present banding system is described. The antenna/controller pod 23 is disposed at the distal end of the antenna cable 24 and includes the removable tag 25 and holes 75. The tag 25 comprises a grip structure that facilitates manipulation and placement of the antenna/controller pod 23 during implantation; after which the tag 25 is removed using a scissors cut. The tag 25 also includes hole 25*b* that allows the use of a suture thread to assist in passing the antenna/controller pod 23 behind the stomach. The holes 75 also are dimensioned to be compatible with standard suture needles from size 1-0 to 7-0 to permit the antenna/controller pod 23 to be sutured to the patient's sternum, thereby ensuring that the antenna/controller pod 23 remains accessible to the external antenna 14 and cannot migrate from a desired implantation site.

As shown in FIG. 9, the antenna/controller pod 23 encloses a printed circuit board 76 that carries the antenna 83 and microcontroller circuitry of the gastric band 21. The antenna 83 receives energy and commands from the external control 10 (see FIG. 1), and supplies those signals to the microcontroller, which in turn powers the motor 66 of the drive element 35. The circuitry of the antenna/controller pod 23 uses the energy received from the incoming signal to power the circuit, interprets the commands received from the external control 10, and supplies appropriate signals to the motor of the drive element 35. The circuit also retrieves information regarding operation of the motor of the drive element 35 and relays that information to the external control 10 via the antenna 83. The circuit board preferably is covered with a water-resistant polymeric covering, e.g., parylene, to permit use in the high (up to 100%) humidity environment encountered in the body.

The antenna/controller pod 23 includes a mechanical closure system that is augmented by silicone glue so that the pod is fluid tight. This silicone glue also is used to protect soldered wires 79 from humidity. The antenna/controller pod 23 preferably is small, e.g., 16 mm×33 mm×4 mm, to ensure compatibility with a standard 18 mm trocar and so as to be compatible with placement on the sternum. The antenna/controller pod 23 preferably has a smooth, atraumatic shape to avoid tissue damage, has good mechanical strength to withstand handling with surgical graspers and to prevent mechanical deformation to the printed circuit board, and has good electromagnetic permeability to allow efficient energy transmission through the antenna/controller pod 23. The antenna/controller pod 23 preferably has a relatively thin planar configuration to avoid rotation of the antenna/controller pod 23 when placed under the skin, and may include holes that permit the antenna/controller pod 23 to be sutured in position.

With respect to FIG. 10, the antenna cable 24 is shown in cross-section. The antenna cable 24 preferably is a coaxial shielded cable encapsulated in a silicone tube 77 to provide biocompatibility. The tube 77 is selected to provide leak-proof encapsulation, with sufficient strength to permit the antenna cable 24 to be manipulated with atraumatic graspers. The braided shield 78 of the antenna cable 24 prevents longitudinal deformation of the antenna cable 24, and surrounds five helically wound insulated wires 79. Four of the wires 79 are used to supply power to the micromotor of the drive element 35; the remaining wire and braided shield 78 are used to supply a signal from the reference position switch to the controller.

Referring to FIGS. 11-19 in order to allow for ready replacement of the antenna/controller pod 23, the antenna cable 24 is selectively coupled to the antenna/controller pod 23 for ready detachment therefrom. Without the provision for selective detachment as provided in accordance with the present invention, malfunction or replacement of the antenna/controller pod 23 would require complete replacement of the gastric band 21. This would necessitate removal of scar tissue attaching the gastric band 21 to the stomach. The antenna cable 24 includes a proximal end 712 which is selectively secured to the distal end 714 of the antenna/controller pod 23. As such, electrical connections between the antenna/controller pod 23 and the antenna cable 24 are also selectively maintained.

In practice, and as applied to the various embodiments discussed below, the antenna/controller pod 23 may be installed in conjunction with the gastric band 21 or the antenna/controller pod 23 may be installed separately from the gastric band 21 and subsequently attached thereto. One advantage of installing the antenna/controller pod 23 separately is that it becomes possible to use a larger size antenna/controller pod and implant it deeper into body tissue. Using the largest size of implantable antenna possible would increase the power coupling efficiency to the external control. The deeper into tissue the antenna is implanted the less efficient the coupling becomes. This can be attributed to both the physical distance as well as dielectric losses exhibited by the tissue which is highly dependent on the transmission frequency and transmission power.

The drawback to a larger size antenna is that it would not be easily introducible into the body or body tissue if integrally attached to the restrictive device and cable. A detachable antenna facilitates implanting the restrictive device and cable prior to connecting the antenna. The cable could then be routed to the position where the antenna is implanted and subsequently connected to the antenna at the remote antenna implant site. The implantation of the antenna/controller pod 23 separately from all other components permits the antenna/controller pod to be constructed in various sizes and shapes to accommodate different desired implantation sites and the required coupling efficiency for the site.

With the foregoing in mind, where the antenna/controller pod 23 and gastric band 21 are implanted together, standard surgical procedures are used. However, where it is desired to separately install the antenna/controller pod 23 and the gastric band 21, the medical practitioner first accesses the body for placement of the antenna/controller pod 23 through a first body opening and similarly accesses the body for implantation of the gastric band 21 through a second spaced body opening. Once the antenna controller pod 23 and the gastric band 21 are properly installed, the antenna cable 24 extending from the gastric band 21 is drawn through the body to a position adjacent the antenna/controller pod 23. At this time, the antenna cable 24 is connected to the antenna/controller pod 23 by the various connection mechanisms discussed below in greater detail. Thereafter, the openings within the body are closed and the gastric band 21 is permitted to operate in a traditional manner.

With this in mind, the following embodiments provide an electromechanical connection between the antenna/controller pod 23 and antenna cable 24 for connecting the gastric band 21 to the antenna/controller pod 23. The connection provides for a fluid tight seal covering and preventing fluid from entering the connection space. The connection may or may not have redundant seals and it may or may not be done with mechanical/electrical connection (one or more steps/motions). By allowing for ready replacement, the antenna/controller pod 23 may be switched out in the event of an electrical or mechanical failure, hardware or software upgrades, and/or feature additions such as pressure sensing, or battery pack.

In particular, the method of implanting the antenna/controller pod and gastric band separately to regulate the functioning of a patient's organ or duct would involve: a) inserting an antenna/controller pod into the patient through a first body opening remote from the patient's organ or duct to be regulated; b) inserting through a second body opening spaced from the first body opening an elongated restrictive device comprising an elongated member having first end and second ends with a fastener disposed on the first end of the elongated member, the fastener configured to engage the second end of the elongated member so that the elongated member forms a ring around the organ or duct to be regulated, a tension element disposed for movement within the elongated member, and a drive element associated with and engaging the tension element for causing the tension element to control the tension applied by the elongated member against the patient's body organ or duct; and c) connecting in situ the antenna/controller pod via a cable to the drive element of the elongated restrictive device in order to control movement of the tension element.

In accordance with a preferred embodiment of the present invention as shown with reference to FIGS. 11, 12, 13, and 14, the distal end 714 of the antenna/controller pod 23 includes a first electrical attachment member 716 and the proximal end 712 of the antenna cable 24 includes a second electrical attachment member 718 cooperating with cable wires 726. The first electrical attachment member 716 includes a first end shaped and dimensioned for selective attachment to the second electrical attachment member 718 and a second end attached to wires 724 of antenna pod 23. In particular, the first electrical attachment member 716 is formed as a ball and the second electrical attachment member 718 is formed as a cup. The ball and cup mate to complete the electrical connection between wires 724 and wires 726 and can only mate in one orientation ensuring proper wire alignment. The first electrical attachment member 716 includes a housing sheath 720 with a housing sheath opening 722 dimensioned to receive proximal end 712 of the antenna cable 24. The housing sheath opening 722 is tapered. As a result, when the proximal end 712 of the antenna cable 24 is inserted into the housing sheath opening 722, a fluid tight friction fit results as the diameter of housing sheath 728 of the proximal end 712 of the antenna cable 24 is forced to fit within a smaller diameter housing sheath opening 722. When the first and second electrical attachment members 716, 718 are coupled, the housing sheath 720 of the first attachment member 716 mates with the housing sheath 728 of the second attachment member 718 to create a fluid tight seal protecting the electrical components contained with the housing sheaths 720, 728 of the first and second electrical attachment members 716, 718.

It is contemplated the coupling between the proximal end 712 of the antenna cable 24 and housing 720 of the antenna pod 23 could take a variety of forms without departing from the spirit of the present invention. For example, the coupling may include threads as shown in FIG. 16 or a bayonet style connection as shown in FIG. 17.

By providing an antenna/controller pod 23, which is selectively detachable from the antenna cable 24, easy removal of the antenna is possible should the antenna be damaged due to shorting out, hermetic concerns, electronic and/or software upgrades in the future, etc. The provision of the selectively attachable antenna/controller pod 23 also allows for minor revision surgery (that is, close to the surface of the skin) rather than major revision surgery (requiring removal of the entire product). It is further contemplated a selectively detachable antenna/controller pod may also provide the ability to change the size of the antenna such that a larger antenna could be implanted initial to increase transcutaneous coupling efficiency in deeper tissue. When the patient loses a sufficient amount of weight the antenna/controller pod may be replaced with a smaller version. Coupling efficiency will increase as the transmitting and receiving antennas are within closer proximity. A smaller antenna/controller pod may provide more comfort and better aesthetics for the patient.

In practice, it is contemplated that when the antenna/controller pod 23 is detached and replaced or simply detach and reattached, it may be necessary to recalibrate the tightening of the gastric band 21 so that the status of the gastric band 21 is properly linked to the control circuitry maintained within the antenna/controller pod 23.

Figure 15:
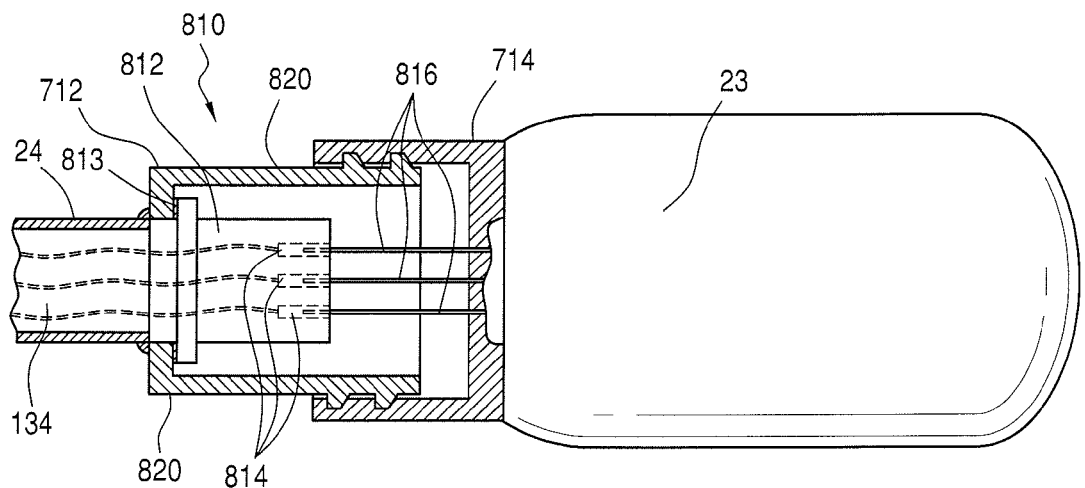
Figure 16:
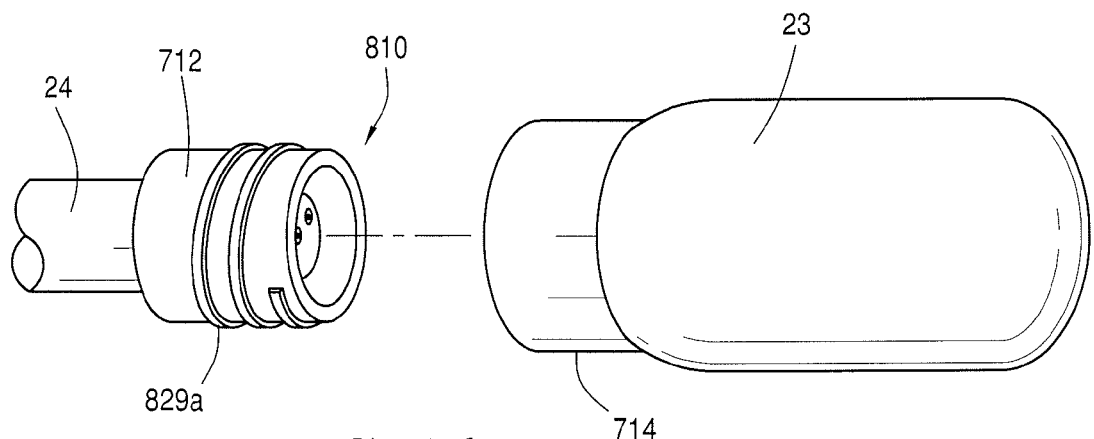
Figure 17:
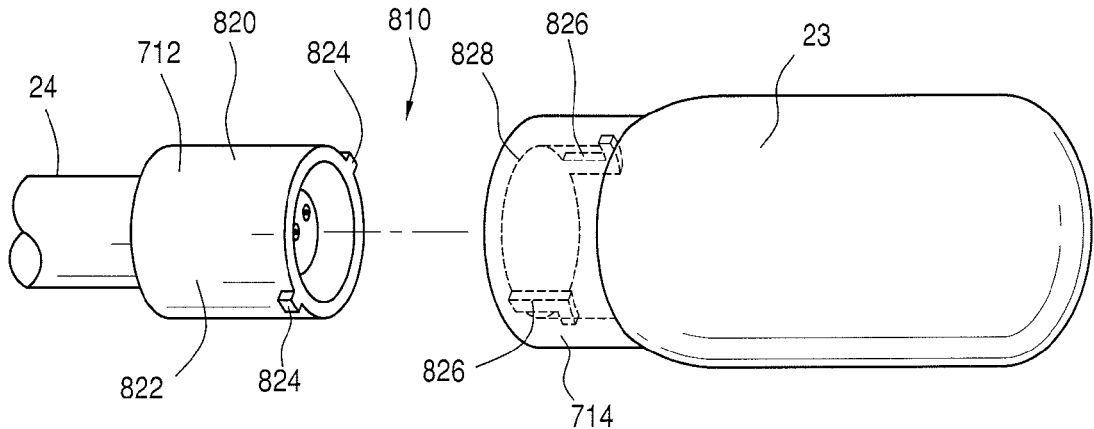

In accordance with an alternate embodiment as shown with reference to FIGS. 15, 16 and 17, the connection of the antenna cable 24 to the antenna/controller pod 23 employs an environmentally sealed housing 810, for example, such connectors as those available from LEMO Inc. Briefly, the connector contains a center portion 812 that houses the wires 134 from the antenna cable 24 and female receptacles, or other electrical connection members, 814 for receiving the male pins 816, or other electrical connection members, from the antenna/controller pod 23. The center portion 812 is housed in a biocompatible housing 820, such as ceramic, titanium, PEEK material or other suitable biocompatible and hermetic material. Pins 816 may be fritted through housing 820 to maintain hermetic sealing of the electronics. Similarly, receptacle pins 814 may be fritted through housing 812. It should also be understood that the female and male pins may be in the opposite configuration.

Referring to FIG. 15, a cross section illustrates the electrical connection and a silicon antenna housing that is locked in place with a threaded connection 829a.

Referring to FIG. 17, the housing 820 of the connector is selectively secured to the antenna/controller pod 23 via a bayonet style connection. Accordingly, the outer wall 822 of the housing 820 is provided with projections 824 shaped and dimensioned for engagement with a slot 826 formed along the coupling member 828 of the antenna/controller pod 23.

In these embodiments the center portion 812 is secured to the housing 820 such that it is free to rotate with respect to the cable housing 820. This allows the electrical connection to remain in a stationary orientation as the bayonet or threads are locked into the antenna/controller pod 23. An o-ring or gasket 813 is located between center portion 818 and cable housing 820 to form a fluid tight seal, but still allow rotation between the parts. An o-ring (not shown), or tube of silicon or o-ring material, is squeezed between the connector housing 820 and housing sheath 720 of the antenna/controller pod 23 upon connection. This will reduce the fluid penetration into the electrical connection, which may degrade and corrode the electrical contacts. It would be advantageous to make the connection in a dry environment and use airtight electrical contacts to minimize fluid ingress at the electrical connection points. It would also be advantageous to use a contact material that is highly tolerant to a salt water (saline) environment, such as gold, platinum, niobium, etc.

Referring now to FIGS. 18 and 19, another embodiment is disclosed. In accordance with this embodiment, a threaded connection 910 is utilized for securing a pod type of antenna/controller pod 923 to the cable 924. The cable 924 is provided with a retaining base 914 at its proximal end 912. The retaining base 914 is shaped and dimensioned such that it may be sutured to the fascia. The antenna/controller pod 923 is then selectively screwed upon the retaining base 914.

As discussed above with respect to FIG. 1, the gastric band 21 according to the present invention provides an integrated system for regulating food ingestion in the stomach of a patient, wherein variation of the diameter of the gastric ring 22 may be adjusted without any invasive surgical intervention. To accomplish this, the drive element 35 is linked to the subcutaneous antenna/controller pod 23 to receive a radio frequency control and power signal. In accordance with a preferred embodiment, the motor 66 of the drive element 35 has no internal energy supply, but rather is powered by the receiving circuit of the antenna 83 through a rechargeable energy storage device, such as a capacitor. In particular, the receiving circuit converts radio frequency waves received from the external control 10 via the antenna into a motor control and power signal. In accordance with an alternate embodiment, it is contemplated the drive element may be driven via an implantable rechargeable battery.

Figure 20:
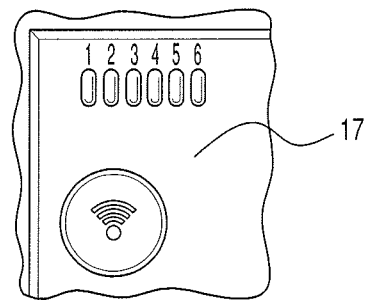

Referring to FIG. 20, a preferred embodiment of the circuitry employed in the external control 10 and the gastric band 21 of the present invention is described, based on the principle of passive telemetry by FM-AM absorption modulation. The external control 10 is shown on the left hand side of FIG. 1, and includes a microprocessor 80 coupled to the control panel 12 and the display screen 13. The external control 10 produces a signal comprising one or more data bytes to be transmitted to the implantable antenna/controller pod 23 and the drive element 35 (shown on the right hand side of FIG. 1).

The external control 10 includes a modulator 81 for amplitude modulation of the RF wave from the RF generator 82, which signal is emitted by the external antenna 14. The emitted wave is received by the antenna 83 in the antenna/controller pod 23, where the AM demodulator 84 extracts the data bytes from the envelope of received RF signal. The data bytes then are decoded and written into an EEPROM of the microcontroller 85. A special code is used that allows easy decoding of the data by the microcontroller 85, but also provides maximal security against communication failure.

An external oscillator 86, which is a voltage controlled oscillator (VCO), provides a clock signal to the microcontroller 85. The oscillator 86 may consist of for example, a relaxation oscillator comprising an external resistor-capacitor network connected to a discharging logic circuitry already implemented in the microcontroller or a crystal oscillator comprising a resonant circuit with a crystal, capacitors and logic circuits. The former solution requires only two additional components, is suitable when the stability of the frequency is not critical, and has low current consumption; the latter solution provides a more stable frequency, but requires a greater number of additional components and consumes more power. The oscillator 86 preferably comprises the external RC network, due to its simplicity.

The microcontroller 85 interprets the received instructions and produces an output that drives the motor 66 of the drive element 35. As discussed above, the drive element 35 comprises a bi-directional stepper motor 66 that drives the nut 60 through a series of reducing gears. Preferably, the two coils of the stepper motor 66 of the drive element 35 are directly connected to the microcontroller 85, which receives the working instructions from the demodulator 84, interprets them and provides the voltage sequences to the motor coils. When the supply of voltage pulses to the stepper motor 66 stops, the gears are designed to remain stationary, even if a reverse torque or force is applied to the nut 60 by the tension element 32.

As also described above, use of a stepper motor 66 in drive element 35 makes it is possible to obtain positional information on the nut 60 and the tension element 32 without the use of sensors or encoders, because the displacement of the tension element 32 is proportional to the number of pulses supplied to the stepper motor coils As described above, the external control 10 transmits both energy and commands to the implantable controller circuitry in the antenna/controller pod 23. The external control 10 also receives feedback information from the implantable controller that can be correlated to the position of the tension element 32 and the diameter of the ring 22. As will be apparent to one of skill in the art, the external control 10 and the implantable controller are configured in a master-slave arrangement, in which the implantable controller is completely passive, awaiting both instructions and power from the external control 10.

Referring to FIG. 20, some of the safety features of the banding system of the present invention are described. As discussed above, both power and control signals are provided to the implantable controller from the external control 10. Because power is delivered to the implantable controller via magnetic induction, the amount of energy delivered to the controller depends on the quality of the coupling between the external antenna 14 and the antenna circuitry contained within the antenna/controller pod 23.

The quality of the coupling may be evaluated by analyzing the level of the feedback signal received by the external control 10, and a metric corresponding to this parameter may be displayed on the signal strength indicator 17, which includes 6 LEDs (corresponding to six levels of coupling). If the coupling between the antennae 14, 83 is insufficient, the motor 66 of the drive element 35 may not work properly, resulting in an inaccurate adjustment of the gastric band 21.

Accordingly, in a standard mode of operation, adjustment may be made only if the coupling quality is strong enough, as indicated by having at least LED 5 or LED 6 in FIG. 20 illuminated. If, on the other hand, poor coupling exists (e.g., one of the first four LEDs are illuminated) it is still possible to perform some adjustment of the gastric band 21, although the adjustment may be inaccurate.

The design of the external control 10, in combination with the patient microchip card 16 (see FIG. 1), also ensures a high degree of efficacy and safety. First, as contemplated for use with the gastric band 21 of the present invention, the external control 10 is intended primarily for use by a physician in an office or hospital setting, and not by the patient alone. Of course, in alternative embodiments, such as to treat urinary or fecal incontinence, it would be essential to provide an external control 10 for use by the patient. The simplicity of the design of the external control 10 and ease of use would provide no impediment to use by the patient for such embodiments.

As discussed with respect to FIG. 1, patient microchip card 16 stores, among other data, a serial number identifying a corresponding gastric band 21 and the diameter of the ring 22 upon completion of the previous adjustment. When the external control 10 first transmits energy to the implantable controller of the gastric band 21, the gastric band 21 identifies itself to the external control 10. In the standard mode of operation, the serial number stored on the patient microchip card 16 must match that received from the gastric band 21, otherwise no adjustment is permitted.

As a failsafe, however, the physician still may adjust the gastric band 21 even if the patient has lost or misplaced his microchip card 16. In this case, the external control 10 may be set in a "no card mode". In this mode, the information displayed on the display screen 13 of the external control 10 corresponds only to the relative variation of the gastric band 21 during that adjustment session, and is no longer indicative of absolute diameter. When the physician activates this mode, an emergency bit is set in the memory of the implantable controller to indicate the "no card mode". In subsequent adjustment sessions, the implantable controller will signal that the gastric band 21 was adjusted in the "no card mode" and all further adjustments will be reported on a relative basis. If the patient again locates the microchip card 16, the emergency bit may be cleared by fully opening the gastric band 21 and thus reaching the reference contact, which re-initializes the position. Subsequent adjustments will again be managed in the standard mode of operation.

During adjustment of the gastric ring 22, a physician places the external antenna 14 in a face-to-face position on the skin of the patient relative to the antenna/controller pod 23 of the gastric ring 22, and to receive feedback information from which the constricted diameter of the gastric ring 22 may be computed. In accordance with the principles of the present invention, it is possible to vary the diameter of the gastric ring 22 without having to undertake invasive surgical intervention, and this variation may be carried out at will, because multiple control cycles may be carried out at regular or irregular intervals, solely under the control of the treating physician.

The banding system of the present invention is expected to be particularly reliable, relative to previously-known hydraulic bands that can be adjusted by the patient, because only the physician typically will have access to the external control box needed to adjust the ring. For a ring embodiment intended for treatment of morbid obesity, the patient therefore does not have free access to any means to adjust the diameter of the ring.

Moreover, because the gastric band of the present invention provides a precise readout of the current diameter of the ring in the standard mode of operation, it may not be necessary for the patient to ingest a radiographic material (e.g., barium dye) to permit radiographic visualization of the ring to confirm the adjusted size. The process of adjusting the band accordingly may be carried out in a doctor's office, without the expense associated with radiographic confirmation of such adjustments. In addition, the self-blocking configuration of the tension element and nut, in combination with the mechanical nature of the gastric band, overcome problems associated with previously-known hydraulically-actuated gastric band systems.

Figure 21:
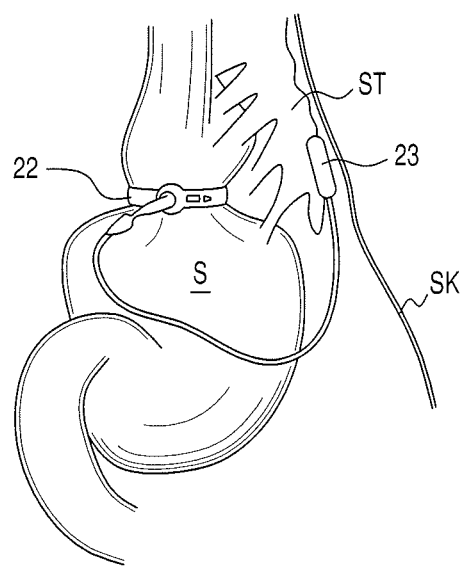
FIG. 21 is a schematic diagram illustrating placement of the implantable portion apparatus of the present invention within a patient.

Referring now to FIG. 21, the gastric band 21 of the present invention is shown implanted in a patient. The ring 22 is disposed encircling the upper portion of the patient's stomach S while the antenna/controller pod 23 is disposed adjacent to the patient's sternum ST. The antenna/controller pod 23 is located in this position beneath the patient's skin SK so that it is easily accessible in the patient's chest area to facilitate coupling of the antenna/controller pod 23 to the external antenna 14 of the external control 10 (see FIG. 1).

As stated above, the telemetrically-powered and controlled ring system of the present invention has numerous applications apart from gastric banding for the treatment of morbid obesity. For example, the ring system of the present invention may advantageously be used for the treatment of fecal incontinence, ileostomy, coleostomy, gastro-esophageal reflux disease, urinary incontinence and isolated-organ perfusion.

For treatment of fecal incontinence, the ring may be used with little or no modifications. In addition, because the ring adjustment procedure will be performed by the patient on at least a daily basis, a portable user-friendly external control may be used. In addition, because the ring will regularly be transitioned between the closed and fully opened position, the patient microchip card is unneeded. Instead, the fully closed position may be stored in the memory of the implantable controller, and read by the external remote at each use (subject to periodic change by the physician).

A similarly modified device could be used by patients who have undergone ileostomy or coleostomy, or disposed surrounding the esophageal junction, to treat gastro-esophageal reflux disease.

For treatment of urinary incontinence, the ring may be further modified to minimize the volume of the ring surrounding the urethra by moving the drive element motor to a location elsewhere in the lower abdomen or pelvis, and coupling the drive element to the motor via a transmission cable.

The present invention also may be beneficially employed to perform isolated-organ perfusion. The treatment of certain cancers requires exposure to levels of chemotherapy agents that are too high for systemic circulation. It has been suggested that one solution to this problem is perform an open surgery procedure in which blood flow to the cancerous organ is stopped and quiescent blood replaced by circulation from an external source containing a desired dose of drug. Individual or multiple rings of the present invention may be used as valves to isolate the cancerous organ and permit perfusion of the organ with high doses of drugs. Such procedures could thus be performed on a repetitive basis without surgery, thereby reducing the trauma and the risk to the patient while improving patient outcomes.

Although particular embodiments of the present invention have been described above in detail, it will be understood that this description is merely for purposes of illustration. Further variations will be apparent to one skilled in the art in light of this disclosure and are intended to fall within the scope of the appended claims.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. Apparatus for regulating the functioning of a patient's organ or duct, comprising:
an elongated member having first end and second ends;
a fastener disposed on the first end of the elongated member, the fastener configured to engage the second end of the elongated member so that the elongated member forms a ring around the organ or duct;
a tension element disposed for movement within the elongated member;
a drive element associated with and engaging the tension element for causing the tension element to control the tension applied by the elongated member against a patient's body organ or duct; and
an antenna/controller pod releasably coupled to the elongated member for control of the drive element, wherein an antenna cable connects the antenna/controller pod to the elongated member, the antenna cable including a proximal end which is selectively secured to a distal end of the antenna/controller pod by threads or a bayonet style connection in a manner maintaining electrical connections between the antenna/controller pod and the antenna cable;
wherein the distal end of the antenna/controller pod includes a first attachment member having a housing sheath with a threads or a bayonet style connection and the proximal end of the antenna cable includes a second attachment member having a housing sheath with a threads or a bayonet style connection, the threads or a bayonet style connection of the first attachment member being shaped and dimensioned for selective attachment to the threads or a bayonet style connection of the second attachment member to create a fluid tight seal protecting electrical components contained within the housing sheath of the first attachment member and the housing sheath of the second attachment member.

2. Apparatus for regulating the functioning of a patient's organ or duct, comprising:
an elongated member having first end and second ends;
a fastener disposed on the first end of the elongated member, the fastener configured to engage the second end of the elongated member so that the elongated member forms a ring around the organ or duct;
a tension element disposed for movement within the elongated member;
a drive element associated with and engaging the tension element for causing the tension element to control the tension applied by the elongated member against a patient's body organ or duct; and
an antenna/controller pod releasably coupled to the elongated member for control of the drive element, wherein an antenna cable connects the antenna/controller pod to the elongated member, the antenna cable including a proximal end which is selectively secured to a distal end of the antenna/controller pod by threads or a bayonet style connection in a manner maintaining electrical connections between the antenna/controller pod and the antenna cable;
wherein the antenna cable includes an environmentally sealed housing supporting a center portion housing wires from the antenna cable and the center portion also includes connection members for receiving connection members of the antenna/controller pod.

3. The apparatus according to claim 2, wherein the connection members of the center portion are female receptacles and the connection members of the antenna/controller pod are male pins.

4. The apparatus according to claim 2, wherein an outer wall of the housing of the antenna cable is provided with projections shaped and dimensioned for engagement with a slot formed along a coupling member of the antenna/controller pod.

5. The apparatus according to claim 2, wherein the center portion of the antenna cable is secured to the housing such that it is free to rotate with respect to the housing.

6. A method for implanting an apparatus for regulating the functioning of a patient's organ or duct, comprising:
inserting an antenna/controller pod into the patient through a first body opening remote from the patient's organ or duct to be regulated;
inserting through a second body opening spaced from the first body opening an elongated restrictive device comprising:
an elongated member having first end and second ends with a fastener
disposed on the first end of the elongated member, the fastener configured to engage the second end of the elongated member so that the elongated member forms a ring around the organ or duct to be regulated;
a tension element disposed for movement within the elongated member; and
a drive element associated with and engaging the tension element for causing the tension element to control the tension applied by the elongated member against the patient's body organ or duct; and
connecting in situ the antenna/controller pod via a cable to the drive element of the elongated restrictive device in order to control movement of the tension element.

7. Apparatus for regulating the functioning of a patient's organ or duct, comprising:
an elongated member having first end and second ends;
a fastener disposed on the first end of the elongated member, the fastener configured to engage the second end of the elongated member so that the elongated member forms a ring around the organ or duct;
a tension element disposed for movement within the elongated member;
a drive element associated with and engaging the tension element for causing the tension element to control the tension applied by the elongated member against a patient's body organ or duct; and
an antenna/controller pod releasably coupled to the elongated member for control of the drive element, wherein an antenna cable connects the antenna/controller pod to the elongated member, the antenna cable including a proximal end which is selectively secured to a distal end of the antenna/controller pod in a manner maintaining electrical connections between the antenna/controller pod and the antenna cable;
wherein the distal end of the antenna/controller pod includes a first attachment member having a housing sheath with a coupling member and the proximal end of the antenna cable includes a second attachment member having a housing sheath with a coupling member, the coupling member of the first attachment member being shaped and dimensioned for selective attachment to the coupling member of the second attachment member to create a fluid tight seal protecting electrical components contained within the housing sheath of the first attachment member and the housing sheath of the second attachment member.

* * * * *